US005777201A

United States Patent [19]
Poutre et al.

[11] Patent Number: 5,777,201
[45] Date of Patent: Jul. 7, 1998

[54] MODIFICATION OF VEGETABLE OILS USING DESATURASE

[75] Inventors: Candace Gloria Poutre; Asha Mchra-Palta, both of Madison, Wis.

[73] Assignee: Agrigenetics, Inc., San Diego, Calif.

[21] Appl. No.: 742,273

[22] Filed: Oct. 31, 1996

Related U.S. Application Data

[63] Continuation of Ser. No. 222,553, Apr. 4, 1994, abandoned, which is a continuation of Ser. No. 850,714, Mar. 13, 1992, abandoned.

[51] Int. Cl.$^6$ ............... A01H 5/00; A01H 5/10; A01H 15/00; A01H 15/82
[52] U.S. Cl. ............... 800/250; 800/205; 800/255; 800/DIG. 69; 800/DIG. 17; 800/DIG. 9; 800/DIG. 14; 800/DIG. 15; 800/DIG. 26; 800/DIG. 52; 800/DIG. 56; 435/172.3; 435/69.1; 435/375
[58] Field of Search ............... 800/205, 250, 800/255, DIG. 17, DIG. 56, DIG. 9, DIG. 52, DIG. 69; 435/172.3, 375, 69.1

[56] References Cited

U.S. PATENT DOCUMENTS 5,057,419 10/1991 Martin et al. ............... 435/134

FOREIGN PATENT DOCUMENTS

| 0255378 | 2/1988 | European Pat. Off. ........ C12N 15/00 |
| WO13972 | 9/1991 | European Pat. Off. . |
| WO18985 | 9/1991 | European Pat. Off. . |
| 9113972 | 9/1991 | WIPO ............... C12N 1/21 |
| 9115578 | 10/1991 | WIPO ............... A01H 1/00 |

OTHER PUBLICATIONS

Polashock, J., et al. "Expression Of The Yeast Delta Nine Fatty Acid Desaturase In Tobacco (Nicotina Tabacum)"; vol. 5, No. 5, Mar. 1991, Bethesda, MD US; pp. A1159.

Polashock, J.J., et al. "Expression Of The Yeast Delta Nine Fatty Acid Desaturase In Nicotina Tabacum"; vol. 100, No. 2, Oct. 1992, Rockville, MD, US; pp. 894–901.

Stukey et al., "Isolation and characterization of OLEI, a gene affecting fatty-acid desaturation from saccharomyces-cerevisiae," (1989), pp. 16537–16544, J. Biol. Chem.

Stuckey, et al., "The OLEI gene of saccharomyces-cerevisiae encodes the delta-9 fatty-acid desaturase and can be functionally replaced by the rat stearoyl-CoA desaturase gene," (1990), pp. 20144–20149, J. Biol. Chem.

Polashok et al., "Expression of the yeast delta 9 fatty-acid desaturase in tobacco (Nicotiana-tabacum)," 1991, p. 5:A1159, FASEB J..

J. Kennell et al. Mol. Gen. Genet., vol. 210 ('87) pp. 399–406.

W. Gordon-Kamm et al. The Plant Cell, vol. 2, (Jul. '90) pp. 603–618.

M. Bustos et al. EMBO Journal, vol. 10, #6 (1991) pp. 1469–1479.

S. Watson, Ch. 15 in *Comand Corn Improvement*, 3rd Ed., Agroyomy Monograph #18, ed. by G. Grpague & J. Dudley; ASA–CSSA–SSSA, Madison WI, 1988 pp. 881–940.

R. Downey et al., Ch. 35 in *Hybridizonim of Crop Plants*, ed. by W. Fehr & H. Hadley, ASA–CSSA, Madison WI, 1980, pp. 495–509.

J. Doyle et al. JBC, vol. 261, #20 (15 Jul. '86) pp. 9228–9238.

J. Doyle et al. J.B.C. 261 (20) 9228–38 ('86).

J. Kennell et al. Mol. Gen. Genet. 210:399–406 ('87).

W. Gordon-Kamm et al. The Plant Cell 2:603–18 ('90).

*Primary Examiner*—Charles C.P. Rories
*Attorney, Agent, or Firm*—Saliwanchik, Lloyd & Saliwanchik

[57] ABSTRACT

Plant seed having yeast delta-9 desaturase gene therein, preferably in association with a suitable promoter and termination sequence. A method for modifying the fatty acid content of seed oil, by transforming seed with yeast delta-9 desaturase.

25 Claims, 4 Drawing Sheets

```
                                                                                              SnaBI                                      BclI
     1   tacttctgttccgtttatatttgtattacgtagaatagaacatcatagtaatagatagtagtgtggtgatcattaaacagcactaaaacattaca                                    99
                                                                                                    SalI       SalI 100   acaaagATGCCAACTTCTGGAACTACTATTGATGACGACCAATTTCAAAGATGACTCTGCGCAGCAGTGCATTGTCGACGAAGTCGACTTA            198
               METProThrSerGlyThrThrIleGluLeuIleAspAspGlnPheProLysAspAspSerAlaSerSerGlyIleValAspGluValAspLeu 199   ACGGAAGCTAATATTTGGCTACTGTTTGAATAGAAGCACCAAGAATTGTCAACGTTTTGGTTCTTAATGGGCTCCAAGGAAATGGTTCCGTG            297
         ThrGluAlaAsnIleLeuAlaThrGlyLeuAsnLysLysAlaProArgIleValAsnGlyPheGlySerLeuMETGlySerLysGluMETValSerVal
         EcoRI 298   GAATTCGACAAGAAGGAAACGAAAAGAAGTCCAATTTGATCGTCTGTAGAAAAGGACAACCAAGAAAAAGAAGAAGCTAAAACTAAAATTCACATC            396
         GluPheAspLysLysGlyLysAsnGluLeuLysSerAsnLeuAspArgLeuLeuGluLysGluGluAlaLysThrLysIleHisIle
                                 NcoI 397   TCCGAACAACCATGGACTTTGAATAACTGGCACCAACATTGAACATGGTTCTTGTTGTGGTATGCCAATGATTGGTTGGTACTTTGCT               495
         SerGluGlnProThrLeuAsnAsnTrpHisGlnHisLeuAsnTrpLeuAsnMETValLeuValCysGlyMETProMETIleGlyTrpTyrPheAla
                                                                                        BstEII 496   CTCTCTGGTAAAGTGCCTTTGCATTTAAACGTTTTCCGTTTTCTCCGTTTTCTACTACGCCTCGGTGTTTCTATTACTGCCGGTTACCATAGATTA         594
         LeuSerGlyLysValProLeuHisLeuAsnValPheLeuPheSerValPheLeuPheTyrAlaValGlyValSerIleThrAlaGlyTyrHisArgLeu
                  BglII 595   TGGTCTCACAGATCTTACTCCGCTCACTGGCCTCCATTGAGATTATTCTACGCTATCTTCCGTTGTGCTTCCGTTGAAGGGTCCGCTAAATGGGCCAC         693
         TrpSerHisArgSerTyrSerAlaHisTrpProLeuArgLeuPheTyrAlaIlePheTyrAlaIlePheGlyCysAlaSerValGluGlySerAlaLysTrpTrpGlyHis
                                                            EcoRI 694   TCTCACAGAATTCACCATCGTTACACTGATACCTTGAGAGATCCTTATGACGCTCGTAGAGGTCTATGGTACTCCCACATGGATGATGCTTTTGAAG         792
         SerHisArgIleHisHisArgTyrThrAspTyrAspProTyrAspProTyrAspProTyrAspAlaArgArgArgGlyLeuTrpTyrSerHisMETGlyTrpMETLeuLeuLys
                                                                                                              HpaI 793   CCAAATCCAAAATACAAGGCTAGAGCTGATATTACCGATGATTGGACCATTAGATTCCAACAGACAGACTACATCTTGTTGATGTGTTA              891
         ProAsnProLysTyrLysAlaArgAlaAspIleThrAspAspTrpThrIleArgPheArgGlnHisArgHisTyrIleLeuLeuMETLeuLeu
```

892 ACCGCTTTCGTCATTCCAACTCTTATCTGTGGTTACTTTTTCAACGACTATATGGGTGGTTGATCTATGCCGGTTTATTCGTGTCTTTGTCATTCAA 990
    ThrAlaPheValIleProThrLeuIleCysGlyTyrPheAsnAspTyrMETGlyGlyLeuIleTyrAlaGlyPheIleArgValPheValIleGln

991 CAAGCTACCTTTGCATTAACTCCTTGGCTCATTACATCGGTACCAACCATTCGATGACAGAAGAACCCCTCGTGACAACTGATTACTGCCATTGTT 1089
    GlnAlaThrPheCysIleAsnSerLeuAlaHisTyrIleGlyThrGlnProPheAspAspArgArgThrProArgAspAsnTrpIleThrAlaIleVal
    BstEII                                                                 EcoRI

1090 ACTTTCGGTGAAGGTTACCATAACTTCCACCACGAATTCCAACTGATTACGAAAACGCTATTAAGTGGTACCAATACGACCCAACTAAGGTTATCATC 1188
     ThrPheGlyGluGlyTyrHisAsnPheHisHisGluProThrAspTyrArgAsnAlaIleLysTrpTyrGlnTyrAspProThrLysValIleIle

1189 TATTTGACTTCTTAGTTGGTCTAGATACGACTTGAAGAAATTCTCAAATGCTATTGAAGAAGCCTTGATTCAACAAGAACAAAAGAAGATCAAT 1287
     TyrLeuThrSerLeuValGlyLeuAlaGlyLeuAlaTyrAspLeuLysLysPheSerGlnAsnAlaIleGluGluAlaLeuIleGlnGluGlnLysLysIleAsn

1288 AAAAAGAAGGCTAAGATTAACTGGGTCCAGTTTGACTGATTGCCAATGGGACAAACAAACCTTCTTGGCTAAGTCTAAGGAAAAACAAGGTTTG 1386
     LysLysLysAlaLysIleAsnTrpValGlnPheAspLysGlnThrPheLeuAlaLeuAlaSerLysGluAsnLysGlyLeu
                                                                              HphI

1387 GTTATCATTCTGGTATTGTTCACGACGTATCTGTTATATCTCTGAACATCCAGGTGGTGAAACTTAAATACTGCATTAGTAAGGACGCTACC 1485
     ValIleIleSerGlyIleValHisAspValSerValSerGlyTyrIleSerGluHisProGlyGlyGluThrLeuIleLysThrAlaLeuGlyLysAspAlaThr

1486 AAGGCTTTCAGTGGTGTGTCTACCGTCACTCAAATGCCGCTCACTCAAATGTCTGGCTGTTATCAAGAAAGTAAGAACTCTGCT 1584
     LysAlaPheSerGlyValValTyrArgHisSerAsnAlaAlaGlnAsnValLeuAlaAspMETArgValAlaValIleLysGluSerLysAsnSerAla

1585 ATTAGAATGGCTAGTAAGAGAGGTGAAATTCTACGAAACTGGTAAGTTCTTTtaagtatcacattacaataacaaaactgcaactaccataaaaaaat 1683
     IleArgMETAlaSerLysArgGlyGluIleTyrGluThrGlyLysPhePhe .
                                                       BspHI 1684 tgaaaaatcataattaaaaaaaaaaatcaattgaattttttttcttttttttcatgattacgttttgacattttttctcttattacgatta 1782

MODIFICATION OF VEGETABLE OILS USING DESATURASE

This application is a continuation of application Ser. No. 08/222,553, filed Apr. 4, 1994, now abandoned, which is a continuation of application Ser. No. 07/850,714 filed Mar. 13, 1992, now abandoned.

FIELD OF THE INVENTION

The present invention relates to a plant seed containing the yeast delta-9 desaturase gene, and to a method for modifying the fatty acid content of seed oil using the desaturase gene.

More specifically, the present invention is directed to a plant seed, such as a *Brassica* or *Zea mays* seed, containing the yeast delta-9 desaturase gene under the control of a promoter which causes expression of the gene in the seed and, as a corollary, to a method of modifying the seed oil fatty acid content using the desaturase gene.

DESCRIPTION OF BACKGROUND AND RELEVANT INFORMATION

Vegetable oils are used not only in the food industry, but increasingly in the chemical industry as well, and are starting to find their way into industrial applications as alternatives to more conventional lubricating fluids. The utilization of the oils depends principally on their compositions. Triglycerides comprise the bulk of vegetable oil (about 95%), but a number of other important lipids are also present, such as phospholipids, free fatty acids, waxes, and sterols. A variety of other components, such as anti-oxidants, may also be present which, while occurring in relatively minor amounts, may nonetheless have a significant impact on the characteristics and, hence, utility of the oils.

The characteristics of triglycerides depend in large measure upon their constituent fatty acids. Because the fatty acids which occur naturally in agronomically acceptable strains of seed oil crops frequently render the resulting oil unsuitable for an otherwise attractive use, it is extremely desirable to have the ability to change the oil composition to meet specified parameters.

Modification of vegetable oils may be effected chemically. This approach has been used to obtain a salad/cooking oil which contains saturated fatty acids of less than about 3% (U.S. Pat. No. 4,948,811); the oil may be formed by chemical reaction, or by physical separation of the saturated lipids. A general reference is made to using "genetic engineering" to achieve an oil of the desired characteristics (see column 3, line 58 et seq.). However, there is no detailed disclosure of how any particular oilseed plant could be so modified to provide a vegetable oil of the characteristics desired.

Typically, the fatty acid composition of vegetable oils has instead been modified through traditional breeding techniques. These techniques utilize existing germplasm as a source of naturally-ocurring mutations which affect fatty acid composition. Such mutations are uncovered and selected for by the use of appropriate screening, in conjunction with subsequent breeding. For example, such an approach has been used to decrease the amount of the long chain fatty acid erucate in rapeseed oil (Stefansson, B. R. (1983) in High and Low Erucic Acid Rapeseed Oils, Kramer J. K. G. et al., eds; Academic Press, New York; pp. 144–161), and to increase the amount of the monounsaturated fatty acid oleate in corn oil (U.S. patent application, Ser. No. 07/554,526).

Recently, attempts have been made to increase the pool of available mutations from which to select desired characteristics through the use of mutagens. However, mutagens generally act by inactivation or modification of genes already present, resulting in the loss or decrease of a particular function. The introduction of a new characteristic through mutagenesis thus often depends on the loss of some trait already present. In addition, the achievement of desired goals with mutagens is generally uncertain. Only a few types of modified fatty acid compositions in vegetable oils have been achieved using this approach. One example of such a "created" mutation which affects fatty acid composition is the decrease of polyunsaturated fatty acids, in particular of linoleate and linolenate, in rapeseed oil, with a concommittant increase in the monounsaturated fatty acid oleate (Auld, M., et al., (1992) Crop Sci. in press). Another is the decrease of saturated fatty acids in rapeseed oil (PCT International Patent Application Publication Number WO 91/15578). However, the biochemistry of seed oil synthesis is complex, and not well understood; there may be several mechanisms which contribute to the changes in the fatty acid compositions observed in rapeseed oil (PCT International Patent Application Publication Number WO 91/15578). The use of mutagenesis to affect such changes is essentially random, and non-specific.

The possibility of modifying fatty acid composition through the use of genetic engineering would, in theory, allow the precise, controlled introduction of specific desirable genes, as well as the inactivation of specific undesirable genes or gene products. Thus, novel traits completely independent of genes already present could be introduced into plants, or pre-selected genes could be inactivated or modified. However, one predicate to making effective use of genetic engineering to modify fatty acid compositions is a reasonably accurate model of the mechanisms at work in the plant cell regulating fatty acid synthesis and processing.

It is postulated that, in oilseeds, fatty acid synthesis occurs in the plastid, and that the newly synthesized fatty acids are exported from the plastid to the cytoplasm. Here they are utilized in the assembly of triglycerides, which occurs in the endoreticular membranes.

The major product of fatty acid synthesis is palmitate (16:0), which appears to be efficiently elongated to stearate (18:0). While still in the plastid, the saturated fatty acids may then be desaturated, by an enzyme known as delta-9 desaturase, to introduce one or more carbon-carbon double bonds. Specifically, stearate may be rapidly desaturated by a plastidial delta-9 desaturase enzyme to yield oleate (18:1). In fact, palmitate may also be desaturated to palmitoleate (16:1) by the plastidial delta-9 desaturase, but this fatty acid appears in only trace quantities (0–0.2%) in most vegetable oils.

Thus, the major products of fatty acid synthesis in the plastid are palmitate, stearate, and oleate. In most oils, oleate is the major fatty acid synthesised, as the saturated fatty acids are present in much lower proportions.

Subsequent desaturation of plant fatty acids outside the plastid in the cytoplasm appears to be limited to oleate, which may be desaturated to linoleate (18:2) and linolenate (18:3). In addition, depending on the plant, oleate may be further modified by elongation (to 20:1, 22:1, and/or 24:1), or by the addition of functional groups. These fatty acids, along with the saturated fatty acids palmitate and stearate, may then be assembled into triglycerides.

The plant delta-9 desaturase enzyme is soluble. It is located in the plastid stroma, and uses newly-synthesized fatty acids esterified to ACP, predominantly stearyl-ACP, as substrates. This is in contrast to the yeast delta-9 desaturase enzyme, which is located in the endoplamsic reticular membrane, uses fatty acids esterified to Co-A as substrates, and desaturates both the saturated fatty acids palmitate and stearate.

The yeast delta-9 desaturase gene has been isolated from *Saccharomyces cerevisiae*, cloned, and sequenced (Stukey, J. E. et al., *J. Biol. Chem.* 264 :16537–16544 (1989); Stukey, J. E. et al., *J. Biol. Chem.* 265 :20144–20149 (1990)). This gene has also been used to transform the same yeast strain under conditions in which it is apparently overexpressed, resulting in increased storage lipid accumulation in the transformed yeast cells as determined by fluorescence microscopy using Nile Red as a stain for triglycerides (U.S. Pat. No. 5,057,419). The fatty acid composition was not characterized. This reference contains a general discussion of using information from the isolated yeast delta-9 desaturase gene to first isolate other desaturase genes from yeast, or from other organisms, and then to re-introduce these genes into a yeast or plant under conditions which, it is speculated, could lead to high expression, in order to modify the oil produced and its fatty acid composition (see Example 2, at column 9, lines 24 et seq.). However, this discussion is both general and hypothetical. No actual examples are provided, and the only technique offered for accomplishing this goal is a recitation of classic recombinant DNA methodology without guidance as to specific implementation (see column 10, lines 25 et seq.).

Subsequently, it was reported that the yeast delta-9 desaturase gene had in fact been introduced into tobacco leaf tissue (Polashcok, J. et al., FASEB J. 5:A1157 (1991). Apparently, the gene was expressed in this tissue, as evidenced by a reported ten fold increase in palmitoleic acid and a corresponding decrease in palmitic and stearic acids.

The health value of high levels of monounsaturates, particularly oleic acid, as the major dietary fat constituent has been established by recent studies. Such diets are thought to reduce the incidence of arteriosclerosis that results from diets high in saturated fatty acids. There is accordingly a need for an edible vegetable oil having a high content of monounsaturates. Seed mutagenesis has been used to produce a rapeseed oil with no more than 4% saturated fatty acid content (PCT International Patent Application Publication Number WO 91/15578); the lowest value reported was a single seed value of 2.8% saturated fatty acid content. However, this low saturated fatty acid vegetable oil is limited to rapeseed oil.

Expression of the yeast delta-9 desaturase gene in any plant seed tissue could result in a decrease in the saturated fatty acids, with an increase in monounsaturated fatty acids in the seed oil. In this case, the enzyme is proposed to desaturate those saturated fatty acid which are exported from the plastid and thus no longer a substrate for fatty acid desaturation. Thus, transformation of plants with a yeast delta-9 desaturase gene under conditions in which the gene is expressed in the seed tissue leads to decreased saturated fatty acid seed oil.

In addition, expression of the yeast desaturase gene in plants with unusual fatty acid compositions could result in the increase or appearance of unusual fatty acids is the vegetable oil. For example, expression of the yease delta-9 desaturase gene in seed tissue in which the oil contains high levels of palmitate could result in an increase in the level of palmitoleate. In those tissues in which fatty acid elongation occurs (such as a high erucate rapeseed), longer chain fatty acids with unusual double bonds could accumulate. Such fatty acids include cis-vaccenic (18:1 cis 11), 20:1 cis 13, 22:1 cis 15, and 24:1 cis 17. These fatty acids are of industrial interest. For example, oxidative ozonolysis cleavage of 18:1 cis 11 results in the monobasic C7 fatty acid and the dibasic C10 fatty acid. Both the dibasic and monobasic fatty acids are an industrial raw material and commodity fatty acids. They can be used as replacements, or in situations where a specific functionality is desired.

SUMMARY OF THE INVENTION

There is accordingly provided a plant seed comprising a yeast delta-9 desaturase gene and means for expressing the yeast delta-9 desaturase gene in the plant seed. The means for expressing may comprise a promoter effective to cause expression of the yeast delta-9 desaturase gene in the plant seed, and the promoter may be, for example, a phaseolin promoter, a truncated phaseolin promoter, and a 35S promoter. Preferable the promoter is a seed-specific promoter, and most preferably it is truncated phaseolin promoter.

The plant seed may also contain a termination sequence for the yeast delta-9 desaturase gene, such as a yeast delta-9 desaturase termination sequence, a phaseolin 3' termination sequence, or a ORF 25 3' termination sequence.

The plant seed may be a member of a monocot genus, including Zea and Sorghum, with Zea, and particularly *Zea mays*, being preferred. Alternatively the plant seed may belong to a dicot genus, such as Brassica, Helianthus, Carthamus, Sesamum, Glycine, Arachis, Gossypium, Lesquerella, and Vernonia, in which case Brassica, and particularly *Brassica rapa* and *Brassica napa*, are preferred.

In a further embodiment, the present invention is directed to a method for modifying the fatty acid content of the seed oil of a plant seed by transforming the plant seed to express a yeast delta-9 desaturase gene. The modification may involve increasing the percent content of monounsaturated fatty acid in the seed oil of the plant seed. The monounsaturated fatty acid so affected may have a carbon chain length of from 16 to 24 carbon atoms, such as, for example, cis-9-hexadecanoic acid (palmitoleic acid), cis-9-octadecanoic acid (oleic acid), cis-11-octadecenoic acid (cis-vaccenic acid), cis-11-eicosenoic acid, cis-13-eicosenoic acid, cis-13-docosenoic acid, cis-15-docosenoic acid, cis-15-tetracosenoic acid, cis-17-tetracosenoic acid, and combinations thereof. The monounsaturated fatty acid may also be oleic, palmitoleic, or cis vaccenic acid.

Alternatively, the fatty acid content may be modified by reducing the percent content of saturated fatty acid in the seed oil. The saturated fatty acid may be myristic acid, palmitic acid, stearic acid, eicosanoic acid, docosanoic acid, tetracosanoic acid, and combinations thereof.

In this method, the plant seed to be modified may be selected from the same monocot and dicot genera and species listed above.

The transformation is generally accomplished by adding, to the native DNA of the plant seed, exogenous DNA in the form of yeast delta-9 desaturase gene and a promoter for the yeast delta-9 desaturase gene. Suitable transformation techniques include transformation mediation using Agrobacterium, electroporation, polyethylene glycol (PEG), silicon carbide fiber, particle gun, and direct injection.

In a particular embodiment, the transformation contemplates constructing a vector containing the yeast delta-9 desaturase gene and the promoter, placing the vector into a selected strain of Agrobacterium, and treating selected plant cells with the Agrobacterium under conditions sufficient to result in transfer of at least some of the vectors from the Agrobacterium to the plant cells, whereby the yeast delta-9 desaturase gene (SEQ ID NO:1) is expressed in the plant cells.

In a final embodiment, the present invention is directed to a plant obtained from the plant seed as defined by claim 1, wherein the seeds of the plant comprise a yeast delta-9 desaturase gene and means for expressing the yeast delta-9 desaturase gene in the plant seed.

BRIEF DESCRIPTIONS OF THE DRAWINGS

FIG. 1 shows the DNA sequence and partial restriction map of the yeast delta-9 desaturase gene (SEQ ID NO:1). The coding strand of DNA along with the deduced amino acid sequence (SEQ ID NO:2) of the desaturase gene is shown.

DETAILED DESCRIPTION OF THE PREFERRED EMBODIMENTS

Figure 2A:
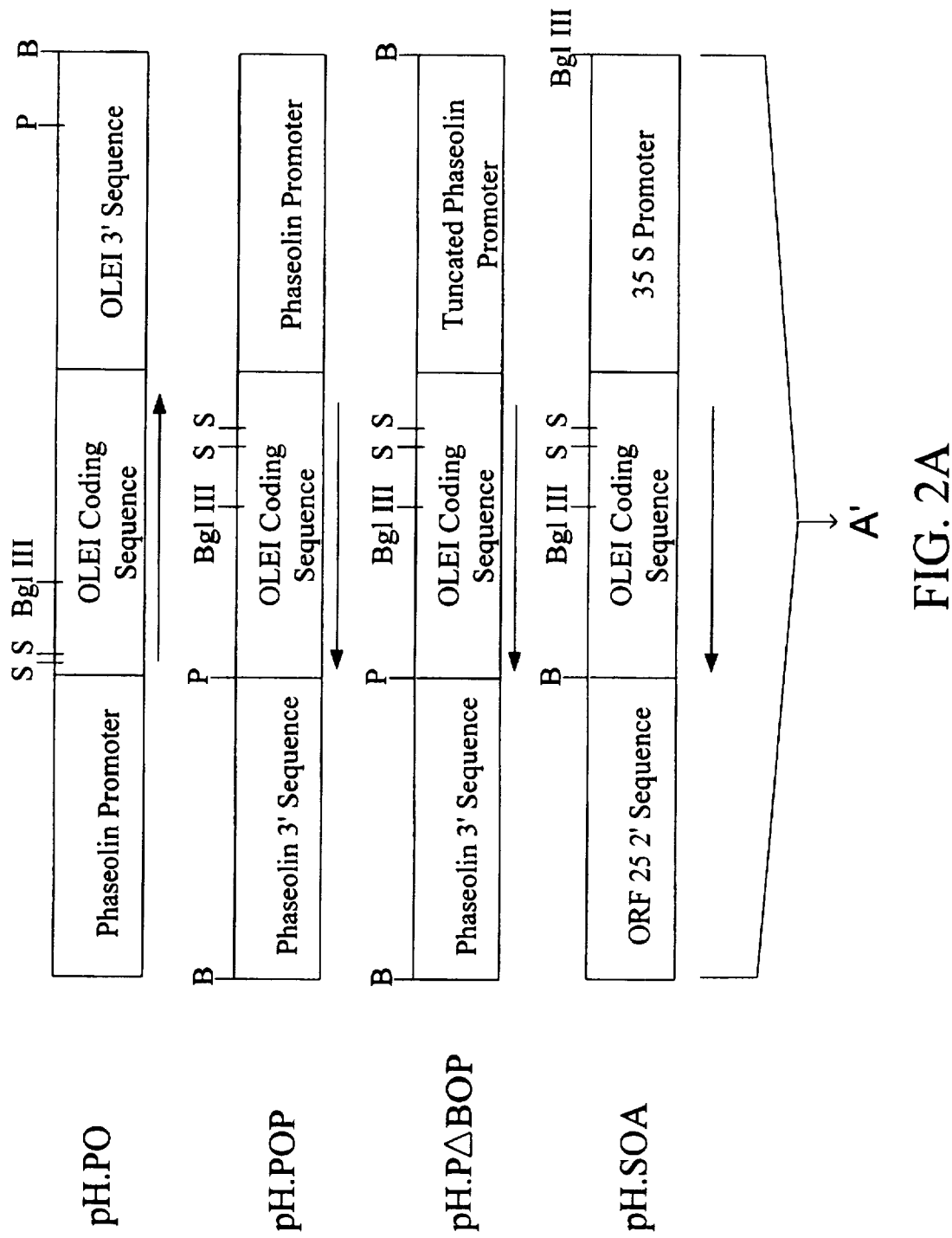
FIG. 2 depicts a scheme of plasmid pH602 and four plant expression cassettes with the yeast delta-9 desaturase gene (SEQ ID NO:1) which were cloned into the unique BgIII site of the plasmid.

In Brief. By means of the present invention, there is provided a plant seed containing and expressing a yeast delta-9 desaturase gene. In addition, there is provided a method for obtaining vegetable oil having an altered fatty acid profile by transforming a plant with a yeast delta-9 desaturase gene under conditions in which the yeast delta-9 gene is expressed in the seed.

In summary form, a yeast delta-9 desaturase gene can be isolated by the following steps. The gene is first cloned by in vivo complementation of a yeast ole1 mutant strain to OLE+ by transformation with a yeast genomic bank made from wild-type yeast DNA. Plasmid-borne complementing sequences can be characterized by restriction mapping, verified by genetic means, and sequenced.

The coding sequence of the gene is placed under the control of regulatory sequences which function in a plant seed, and is then moved into plant transformation vectors. These constructs, with a suitable selectable marker to select for positive transformants, are then used to transform plant tissue. The resulting calli are regenerated into plants; tissue samples from these plants are screened by at least one molecular or biological assay to determine which individuals actually contain a yeast delta-9 desaturase gene.

Those transformants which contain the yeast delta-9 desaturase are grown to maturity and allowed to set seed. The expression of the yeast delta-9 desaturase gene in the seed is determined by mRNA analysis, such as with a PCR assay, and/or by protein analysis, such as by a Western assay. In addition, the fatty acid composition of the mature seeds is determined to identify any novel fatty acid composition produced in response to the presence of the yeast delta-9 desaturase in the seeds. Those seeds showing altered fatty acid composition are germinated, and the stability and genetics of the observed trait(s) characterized by the proper genetic crosses.

Each of the aspects of the invention will now be discussed in greater detail.

The majority of the DNA and yeast genetic manipulations described below are standard, well-established protocols and can be found in several protocol manuals (Sherman, F et al (1986) Laboratory Course Manual for Methods in Yeast Genetics. Cold Spring Harbor Laboratory Press, NY; Sambrook, J et al (1989) Molecular Cloning, A laboratory Manual, Cold Spring Harbor Laboratory Press, New York; and Methods in Enzym 152: Guide to Molecular Cloning Techniques, Berger, SL and Kimmel, AR, eds (1987). DNA can be sequenced by several methods, including for example the Sanger method, using the protocol for double-stranded templates as per the manufacturer's (U.S. Biochem. Corp., Cleveland, Ohio) instructions.

A delta-9 desaturase gene from yeast can be isolated by the following steps. A yeast strain is created which is suitable for transformation and complementation. Such a strain must be deficient in delta-9 desaturase activity and thus require exogenous unsaturated fatty acids for growth. In addition, the strain may have a second characteristic or marker to allow for the selection of transformed cells. A genomic bank of wild type yeast DNA is then used to transform the yeast strain deficient in delta-9 desaturase activity. Those strains in which restoration of the delta-9 desaturase function was observed (ie, which exhibited a wild-type phenotype and no longer required exogenous fatty acids for growth) are presumed to contain the yeast delta-9 desaturase gene. The recombinant plasmid inserts which putatively contain the delta-9 desaturase gene are then isolated. A restriction map of the insert is prepared, and can be compared to a published map (Stukey, JE (1989) J. Biol. Chem. 264: 16537–16544). Finally, the identity of the gene is verified by standard genetic analysis.

The insert DNA is then subcloned and sequenced to locate and characterize the coding region of the yeast delta-9 desaturase gene. The coding region is moved into plant expression cassettes after selecting the proper regulatory sequence(s) for desired expression. Regulatory sequences include both promoter and termination sequences.

Possible regulatory sequences include, but are not limited to, any promoter already shown to be constitutive for expression, such as those of viral origin (CaMV 19S, TMV, AMV) or so-called "housekeeping" genes (ubiquiton, actin, tubulin) with their corresponding termination/polyA+ sequences. Also, seed- and/or developmentally- specific promoters, such as those from plant fatty acid/lipid biosynthesis genes (ACPs, acyltransferases, desaturases, lipid transfer protein genes) or from storage protein genes (zein, napin, cruciferin, conglycinin, lectin genes), with their corresponding termination/polyA + sequences can be used for targeted expression. In addition, the gene can be placed under the regulation of inducible promoters and their termination sequences so that gene expression is induced by light (rbcS-3A, cab-1), heat (hsp gene promoters) or wounding (mannopine, HRPGs). It is clear to one skilled in the art that a promoter may be used either in native or truncated form, and may be paired with its own or a heterologous termination/polyA + sequence.

In addition, the yeast delta-9 desaturase gene product may be localized to a specific organelle in the plant seed by ligating DNA coding for peptide leader sequences to the desaturase gene. Such leader sequences are obtained from several genes of either plant or other sources. These genes encode cytoplasmically-synthesized proteins directed to, for example, mitochondria (the F1-ATPase beta subunit from yeast or tobacco, cytochrome c1 from yeast), chloroplasts (cytochrome oxidase subunit Va from yeast, small subunit of rubisco from pea), endoplasmic reticulum lumen (protein disulfide isomerase), vacuole (carboxypeptidase Y and proteinase A from yeast, phytohemagglutinin from French bean), peroxisomes (D-aminoacid oxidase, uricase) and lysosomes (hydrolases). These constructs may be used with the corresponding native promoter or with any of the suggested promoters mentioned above.

A selectable marker for optimum transformation selection is also chosen. Such markers are typically genes which encode for resistance to various toxic chemicals such as antibiotics and herbicides; the resistance is usually conferred by enzymes which typically render the chemical non-toxic. Such toxic chemicals include, for example, hygromycin, kanamycin, methotrexate, and phosphinothricin. Enzymes which confer resistance to these chemicals are hygromycin phosphotransferase, neomycin phosphotransferase, dihydrofolate reductase, and phosphinthricin acetyl transferase. Genes which code for resistance are well known to those of ordinary skill in the art of plant transformation. Plants transformed with such genes are able to grow in the presence of the toxic compound, while non-transformed plants are not. Therefore, such genes serve both as a means of selecting transformed plants and as a marker for transformation, indicating that transformation has occurred.

Finally, the plant expression cassette containing the yeast delta-9 desaturase gene is moved into the vector which also contains the selectable marker for use in plant transformation. The selectable marker is typically under the control of a constitutive promoter as are described above. The vector is constructed in such a manner that both the yeast delta-desaturase gene and the marker gene are transferred together into the plant genome.

Plant tissue for use in transformation may be obtained from any suitable oilseed plant. Such plants may be found in the genera Brassica, Helianthus, Carthamus, Sesamum, Glycine, Arachis, Gossypium, Ricinus, Linum, Cuphea, Euphorbia, Limnanthes, Crambe, Lesquerella, Vernonia, Simmondsia, Olea, Papaver, Elaeis, Cocos, and Zea. Appropriate plant tissue includes but is not limited to leaves, hypocotyls, cotyledons, stems, callus, single cells, and protoplasts.

Transformation techniques are well known to those skilled in the art of plant transformation, and include transformation mediated by Agrobacteria, electroporation, polyethylene glycol (PEG), silicon carbide fibers, direct injection and a particle gun. These methods are various means to introduce foreign DNA into plant cells. Once in the cell, a portion of the DNA carrying both the yeast delta-9 desaturase gene and the selectable marker are incorporated into the plant genome via the transfer functions included in the DNA.

Transformed callus tissue is selected by growth on selection medium (eg. medium which contains a toxic chemical and for which the transformed plant contains a resistance gene, by virtue of its transformation). Transformed plants are regenerated and screened for the presence of the yeast delta-9 desaturase gene. This involves analyzing tissue by at least one molecular or biological assays to determine which, if any, transformants contained yeast delta-9 desaturase specific mRNA or DNA sequences. These assays include assays of the tissue for the expression of the resistance gene enzyme, and assays of the tissue for the presence of the yeast delta-9 desaturase DNA by for example, a Southern assay or a PCR assay.

Those plants which are positive for the yeast delta-9 desaturase gene are grown to maturity, pollinated, and allowed to set seed. Seed obtained from transformed plants are analyzed for the expression of the yeast delta-9 desaturase gene by both looking for the protein encoded by the gene, as for example via a Western analysis, and for the phenotype of altered fatty composition as a result of the activity of the desaturase.

A Western analysis determines the presence of a protein encoded and expressed by the yeast delta-9 desaturase gene, and is utilized to detect expression of the gene in plant seed tissue. The assay requires the use of antibodies to the yeast delta-9 desaturase to detect the presence of the protein. Antibodies specific for the yeast delta-9 desaturase protein, which has not been previously purified, are prepared as follows. The coding sequence for the yeast delta-9 desaturase enzyme is cloned into an expression vector (for example, pMAL-p, pMAL-cRI, from New England Biolabs). The resulting protein is isolated and purified according to the manufacturers instructions. Antibodies are then generated to the delta-9 desaturase enzyme by conventional techniques. The specificity of the antibodies to the delta-9 desaturase enzyme is determined by ELISA assays.

The fatty acid composition of either whole or half-seeds, obtained from either control or transgenic plants, are determined by extracting the oil, preparing fatty acid methyl esters, and then separating and quantitating the fatty acid methyl esters by conventional procedures. Novel fatty acid characteristics are determined by comparing the fatty composition of the transgenic seeds to those of the parent plant.

The genetic stability and inheritance of the novel fatty acids traits are determined by classic genetic crosses. The trait(s) conferred by the yeast delta-9 desaturase gene may be transferred into other agronomically acceptable cultivars by standard breeding technology.

EXAMPLE 1

Gene Cloning, Isolation, and Sequencing a. Gene Cloning and Isolation

The delta-9 desaturase gene (SEQ ID NO:1) was cloned in yeast by complementation using a 2-micron vector and looking for cosegregation of markers. A genomic bank of wild type yeast DNA from Saccharomyces cerevisiae strain X2180-1A (the Yeast Genetic Stock Center, Berkeley, Calif.) was prepared in the yeast autonomous plasmid, YEp13. This plasmid transforms at a high efficiency and replicates independently of the chromosomes to a high copy number. YEp13 contains a wild type LEU2 gene for selection of transformants and is mitotically unstable when grown under nonselective conditions. Upon transformation into E. coli, the bank gave $1.7 \times 10^4$ independent transformants, well above the $9.5 \times 10^3$ figure calculated as necessary to result in a 99% probability that a copy of the yeast delta-9 desaturase gene was contained in the bank.

A yeast strain suitable for transformation was constructed by mating two haploid yeast strains and analyzing the resultant haploid spores. One strain was found to contain both mutations (ole1/leu2) needed for complementation. A yeast transformation was performed and transformants selected for both the LEU2 marker contained on the plasmid and for wild type desaturase activity by growth on medium lacking oleate. In this way, 450 transformants which were phenotypically wild type for both LEU2 and desaturase activity were obtained. These transformants were next grown under nonselective conditions, thereby inducing mitotic instability, and then screened for co-loss of the LEU2 plasmid marker and desaturase activity. Co-loss of markers indicated that the desaturase activity was plasmid-borne and not a chromosomal revertant to wild type.

In this way, several plasmid-borne inserts that restored wild-type function when present in mutant yeast cells were identified. A 5.7 kb Hind III fragment was found to be common to most of the inserts, and restriction map analysis of the insert indicated extensive homology to that of the published restriction map (Stukey, J. E. et al (1989) J. Biol. Chem. 264: 16537–16544). The major difference between the two maps is that the published insert is a 4.8 kb Hind III fragment, compared to the 5.7 kb Hind III fragment isolated here. However, the region has been shown to be polymorphic in various yeast strains, including the progenitor strain of the strain from which the genomic bank was made (Stukey, J. E. et al, supra). Additionally, the restriction map is highly conserved in the putative yeast delta-9 desaturase coding region in the insert; the difference in size is due to downstream sequences outside the coding region.

An attempt was made to identify, by Southern analysis, plant DNA sequences that showed homology to the yeast desaturase gene. Genomic DNA from Brassica napus, Brassica rapa, Arabidopsis thaliana, soybean, and maize was digested with each of three restriction enzymes and blotted to a membrane; the membrane was then probed with two random-primer labeled subcloned inserts which contain only open reading frame sequences from the yeast delta-9 desaturase gene. After hybridization, the filter was washed sequentially under increasingly stringent conditions, in order to determine if the signal-to-noise ratio of any homology could be reduced enough to make screening a genomic bank using the same probe feasible. Using the least stringent wash conditions, faint bands could be seen for all the genomes, but, not unexpectedly, heavy background was observed. Under the most stringent (i.e., "normal") wash conditions, the background was noticeably reduced; however, under these conditions, only the maize and the soybean DNA showed obvious bands which were still very faint, especially when compared to those in the yeast DNA.

These data indicate that the yeast delta-9 desaturase gene (SEQ ID NO:1) has little homology to its corresponding gene in Brassica, at least at the DNA level. Because the yeast delta-9 desaturase has both a different location (microsomal vs. chloroplastic) and substrate specificity (fatty acyl-CoA thioesters vs. fatty acyl-ACP thioesters) than does the plant enzyme, it is not unexpected that the two enzymes, despite their similar function, may show little homology at either the DNA or protein level.

Gene disruption studies corroborated the complementation results which indicated that the cloned gene (SEQ ID NO:1) was in fact the yeast delta-9 desaturase gene. A construct was made which inserted a functional LEU2 gene into the coding region of the putative yeast delta-9 desaturase gene (SEQ ID NO:1), thereby disrupting the cloned gene. Using standard yeast genetic techniques, the chromosomal copy of the cloned gene was replaced with the LEU2-disrupted version and the resulting cells were then analyzed for their ability to grow without supplemental oleic acid. In this analysis, if the cloned gene (SEQ ID NO:1) was not the yeast delta-9 desaturase, then its disruption shouldn't affect fatty acid biosynthesis. If the cloned gene (SEQ ID NO:1) was the yeast delta-9 desaturase, then its disruption should result in cells that cannot make oleic acid and therefore require a supplemental source. In fact, yeast cells verified by Southern analysis to contain the disrupted gene cannot grow without supplemental oleic acid.

b. Gene Sequencing

Restriction fragments of the yeast delta-9 desaturase gene (SEQ ID NO:1) produced by digests with several different enzymes were subcloned into the vector pUC18. These fragments were sequenced using double stranded templates with Sequenase (USB) according to the manufacturer's instructions. The results are presented in FIG. 1 (SEQ ID NO:1).

DNA sequence analysis of the cloned insert identified an open reading frame of 1530 bp with a TATAA sequence, the preferred promoter sequence in yeast, located at −30 from the first ATG of the predicted protein which is generally used as the initiation codon of a peptide in yeast. Northern analysis demonstrated that DNA sequences from the open reading frame hybridized to a polyadenylated mRNA of approximately 2.0 kb. The transcript size observed is a good fit for a 1530 bp coding sequence, allowing adequate room for a 3' polyA+ tail, and suggests that the transcript, like most yeast mRNAs, contains no introns.

The 1530 bp coding region of the cloned gene (SEQ ID NO:1), assuming the translational start is the first ATG in the reading frame after the TATAA box, codes for a protein of 510aa (SEQ ID NO:2). Homology searches of known protein data banks have shown that the predicted amino acid sequence of the yeast delta-9 desaturase gene is homologous to both the rat and mouse stearyl-CoA desaturase proteins. Interestingly, homology to both mammalian proteins starts at around 42aa and ends at 397aa. Although the sequence of the cloned yeast delta-nine desaturase gene (SEQ ID NO:1) isolated from Saccharomyces cerevisiae strain X2180-1A is very similar in sequence to that reported isolated from the strain R 254 (originally designated AB320) (Stukey, J. E. et al (1990) J. Biol. Chem. 265: 20144–20149), there is at least one amino acid difference between the two coding regions: the published sequence reports a met at amino acid position 304, as opposed to a leu at the same position observed here.

The data obtained from gene complementation studies, gene disruption studies,and sequence analysis have demonstrated that the cloned gene (SEQ ID NO:1) was the yeast delta-nine desaturase.

EXAMPLE 2

Vector Construction

Four expression vectors were constructed, in which the yeast delta-nine desaturase gene was placed under the control of different promoters and followed by different termination/poly-adenylation sequences. The vector used for plant transformation contained both the desired selectable marker and the yeast delta-9 desaturase gene expression cassette.

Figure 2B:
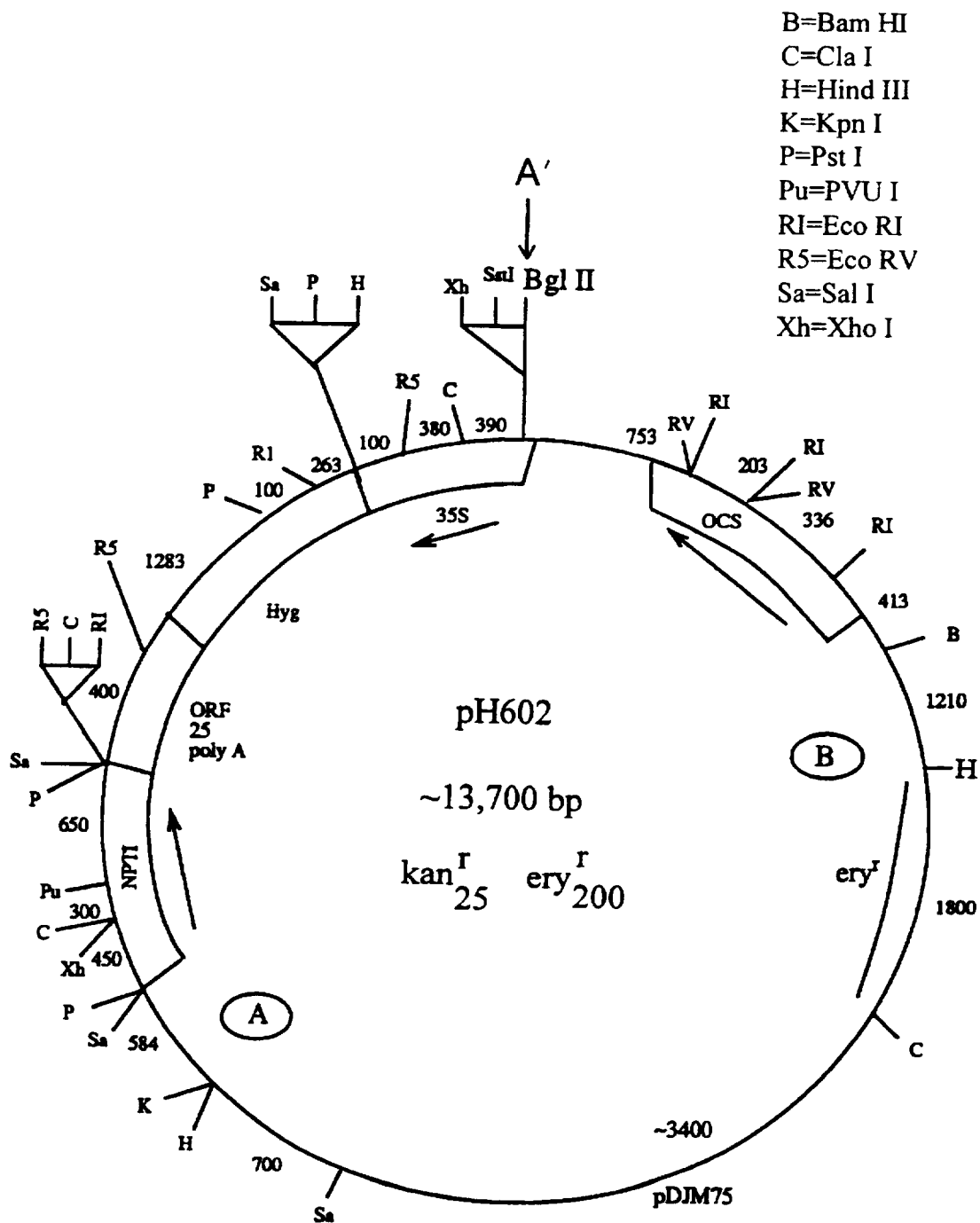

The transformation vector into which the yeast delta-9 desaturase gene expression cassettes were placed is pH602 (see FIG. 2; REF). This vector is a micro Ti plasmid binary vector similar to plasmid pH575 described previously (Hoffman, L. M. et al (1987) EMBO J. 6: 3213–3221) except that it contains as a selectable marker the hygromycin phosphotransferase (HPT) gene instead of a neophosphotransferase II (NPTII) gene (Murray, E. E. et al (1991) Plant Mol. Biol. Reporter 16: 1035–1050). The HPT gene, which confers resistance to the antibiotic hygromycin, is under control of the constitutive promoter CaMV 35S.

In order to obtain expression of the yeast delta-9 desaturase gene (SEQ ID NO:1), the gene was put under the control of a seed-specific phaseolin promoter, obtained from the French bean, Phaseolus vulgaris (REF). Because seed oil accumulation occurs earlier than does the accumulation of seed storage protein during seed development and maturation, the phaseolin promoter is not optimal in terms of temporal regulation. Therefore, the gene was put under the control of a modified phaseolin promoter designed to be expressed earlier than the native phaseolin (Bustos et al (1991) EMBO J. 10: 1469–1479), as well as under the control of the constitutively expressed CaMV 35S promoter.

a. pH.PO

In this vector, the yeast desaturase gene (SEQ ID NO:1) was placed under the control of a seed specific promoter, the seed storage protein phaseolin promoter, and was followed by the yeast desaturase termination sequences.

The vector pSPPneo contained a genomic phaseolin gene and was the source of the promoter used in this construct. The vector was digested with EcoR1 and Sca1; the resulting 1.4 kb EcoR1-Sca1 fragment which contained the phaseolin promoter along with a multiple cloning site was isolated and cloned into pUC18, resulting in the vector designated scp5'phas.

The next step removed the multiple cloning site from the phaseolin promoter. scp5'phas was digested with EcoR1 and EcoRV, both ends were filled in, and the vector religated. The resulting vector was designated scp5'phas-delta, and contained the phaseolin promoter region minus the multiple cloning site.

A 5.8 kb HindIII fragment of yeast genomic DNA that contained the yeast desaturase gene (SEQ ID NO:1) (see above) was isolated and cloned into the HindIII site of pUC18, resulting in the vector designated pUC26A. A 3.5 kb SnaB1-Xho1 fragment which contained the entire yeast desaturase coding sequence and termination sequence (SEQ ID NO:1) was then isolated from pUC26A and cloned into the Sma1-Sal1 site of scp5'phas-delta. The resulting vector was designated pPO.

Finally, a 4.5 kb Nhe1-HindIII fragment, which contained the phaseolin promoter and the yeast desaturase coding and termination sequences (SEQ ID NO:1), was isolated from pPO; this fragment was filled in, BamH1 linkers were added, and the fragment was cloned into the BglII site of pH602. The resulting vector was designated pH.PO.

b. pH.POP

In this vector, the yeast desaturase gene (SEQ ID NO:1) was placed under control of the phaseolin promoter and followed by the phaseolin termination sequences.

A 2.6 kb Nhe1-BspH1 fragment from pPO (see above), which contained the phaseolin promoter and the yeast desaturase coding sequence (SEQ ID NO:1), was isolated. The BspH1 site was filled in, Pst1 linkers were added and the fragment was cloned into the Xba1-Pst1 sites of pUC18. The resulting vector was designated pPO-2.

A 1.5 kb Pst1-Sst1 fragment from pSPPneo, which contained the phaseolin 3' terminating sequences, was isolated. The Sst1 site was filled in, Pst1 linkers were added, and the fragment was cloned into the Pst1 site of pPO-2. The resulting vector was designated pPOP.

pPOP was digested with BamH1, and the insert which contained the phaseolin promoter, the yeast desaturase gene, and the phaseolin 3' termination sequence was cloned into the BglII site in pH602. The resulting vector was designated pH.POP.

c. pH.PdeltaBOP

In this vector, the yeast desaturase gene was placed under control of a modified phaseolin promoter and was followed by the phaseolin termination sequences. The phaseolin promoter was modified by truncation, which has been reported to result in earlier expression of genes regulated by the promoter (Bustos et al (1991) The EMBO J 10: 1469–1479).

A 2.0 kb Bcl1-Pst1 fragment from pPO-2 (see above), which contained a truncated phaseolin promoter and the yeast desaturase coding sequence (SEQ ID NO:1), was isolated. The truncated phaseolin promoter contained only about a third, or 295 bp, of the original promoter sequence. This fragment was cloned into the BamH1-Pst1 sites of pUC18. The resulting vector was designated pPOdeltaB.

A 1.5 kb Pst1 fragment, which contained the 3' polyadenylation sequence of the phaseolin gene, was isolated from POP (see above). This fragment was inserted into the Pst1 site of pPOdeltaB, to create a construct containing a truncated phaseolin promoter, the yeast desaturase gene (SEQ ID NO:1), and the phaseolin termination sequence. The resulting vector was designated pPdeltaBOP.

A 3.2 kb BamH1 fragment from pPdeltaBOP, which contained the truncated phaseolin promoter, the yeast desaturase coding sequence (SEQ ID NO:1), and the phaseolin termination sequence, was isolated. This fragment was inserted into the BglII cloning site of pH602. The resulting vector was designated pH.PdeltaBOP.

d. pH.SOA

In this vector, the yeast desaturase gene (SEQ ID NO:1) was placed under control of a constitutive promoter, the 35S promoter, and was followed by the termination sequences from ORF25.

The vector pIC35/A contains the CaMV 35S promoter and the ORF25 polyadenylation sequence; the two are separated by a multiple cloning site. Thus, the strategy for constructing the vector was to move the yeast desaturase gene (SEQ ID NO:1) from pUC26A into pIC35A between the promoter and the termination sequences, and then to move it into the vector pH602.

A 1665 bp BclI-BspH1 fragment from pUC26A, which contained the genomic yeast desaturase coding sequence (SEQ ID NO:1), was isolated; the BspH1 site was filled in and BamH1 linkers added. This fragment was then cloned into the BamH1 site of pIC35A; the resulting vector was designated pSOA. A 3075 Xba1 fragment from pSOA, which contained the 35S promoter, the yeast desaturase gene coding sequence (SEQ ID NO:1) and the ORF25 3' polyadenylation sequence, was isolated; the fragment was blunt-ended with T4 DNA polymerase and cloned into the BglII site of pH602, which had been blunt-ended with T4 DNA polymerase. The resulting vector was designated pH.SOA.

EXAMPLE 3

Vector Transfer to Agrobacterium

All four plasmids described above, pH.PO, pH.POP, pH.PdeltaBOP, and pH.SOA, were moved into the Agrobacterium strain Z707s by tri-parental mating with the E. coli strains DH15 and RK2013 essentially as described (Rogers SG et al (1988) Plant Molecular Biology Manual A2 (Kluwer Academic Publishers, Dordrecht), pp 1–12).

EXAMPLE 4

Rapeseed Transformation

Rapeseed is one of the world's most important oilseed crops. Considerable effort has been made to improve its agronomic qualities by selective breeding techniques. Brassica napus and Brassica rapa constitute the majority of rapeseed production in North America.

Brassica napus is fairly amenable to tissue culture, thus offering a good system for introduction of foreign genes. Transgenic plants of B. napus obtained by Agrobacteria mediated transformation have been previously reported (Pua et al (1987) Bio/Technology 5: 815–817; Fry et el (1987) Plant Cell Reports 6: 321–325; Radke et al (1988) Theor. Appl. Genet. 75: 685–694); and Moloney et al (1989) Plant Cell Reports 8: 238–242). Microinjection (Neuhaus et al (1987) Theor. Appl. Genet. 75: 30–36)) and protoplast electroporation (Guerche et al (1987) Plant Sci. 52: 111–116) techniques have also been used to transform B. napus. Brassica rapa may also be transformed, as was recently reported at by Mehra-Palta et al (1991, Proceedings of the Rapeseed GCIRC Congress, pp 1108–1115).

The plant used in this example of rapeseed transformation was the Brassica napus cultivar Profit. Seeds were obtained both from normal plants, and from plants obtained from a line of previously regenerated plants. This regenerate line of Profit results in plants whose tissue demonstrates an increased frequency of transformation, when the frequency is calculated as the number of transgenic plants obtained from a specified number of tissue explants. Seeds were surface sterilized with 1.05% sodium hypochlorite (20% Chlorox) for 20 minutes and rinsed 3 times with sterile distilled water. These seeds were aseptically germinated on basal medium(BM) in 20×100 mm petri dishes for 4–6 days. The BM consisted of Murashige and Skoog (1962) macro- and micro-elements, with iron at 40 mg/l FeNa2EDTA, and the following constituents (mg/l): myo-inositol, 100; nicotinic acid, 0.1; pyrodoxine HCl, 0.1; thiamine HCl, 0.02; glycine, 0.4; sucrose, 30,000; and Difco bacto agar, 8,000. The seedlings were grown at 25° C. with a photoperiod of 16 hours. Hypocotyl segments (2–3 mm) were excised from 4–6 day old seedlings and pretreated for 24 hours on BM or Gamborgs' B5 (Gamborg et al, 1968) medium containing alpha-napthaleneacetic acid (NAA) at 5 mg/l or 2,4-dichlorophenoxyacetic acid (2,4-D) at 1 mg/l (callusing medium). A sterile filter paper was placed on the medium prior to treatment.

The hypocotyl segments were treated with the Agrobacterium solution (diluted to 10 * 8/ml with liquid basal medium) for 30 minutes and then placed onto the callusing medium for 2–3 days of co-cultivation.

The hypocotyl tissues were transferred to the callusing medium which contained carbenicillin (500 mg/l) and hygromycin (5–10 mg/l). The cultures were maintained at 22°+–2° C. with a 16 hour photoperiod. After 7 days, the hypocotyl segments were transferred to shoot regeneration medium BM or B5, both of which contained BAP (1–4 mg/l), zeatin (0–4 mg/l), silver nitrate (AgNO3, 2.5–10 mg/l), carbenicillin (500 mg/l), and hygromycin (5–10 mg/l). The callusing and regeneration media were solidified with Agarose (SeaKem, 0.5%) or Gelrite (0.2%). The tissues were transferred to fresh selection medium every three weeks. Callus formation occurred after 1–3 weeks of culture, and shoots were formed 3–6 weeks thereafter. These shoots were then transferred to BM containing BAP (0.01–0.1 mg/l) and carbenicillin (100 mg/l) for elongation, and were later rooted on BM with indole butyric acid (IBA, 0.1 mg/l).

EXAMPLE 5

Determination of Plant Transformation

Each regenerated plant which survived on the selection medium was assayed to determine whether it was in fact transgenic by at least one of the following biological and molecular assays.

a. Leaf Disc Assay

The presence and expression of a gene may be determined by an assay of the activity of the protein which is encoded by the gene. The leaf disc assay is a biological assay which detects the activity of the selectable marker gene, HPT (which confers hygromycin resistance to the transformed tissue), by measuring tissue growth in the presence of hygromycin. Since both the HPT gene and the yeast desaturase gene (SEQ ID NO:1) are transferred together on a single piece of DNA, the presence of the HPT gene indicates that the yeast desaturase gene (SEQ ID NO:1) is also present in the tissue assayed, as separately confirmed by PCR analysis (see below).

Small leaf sections (2–3 mm square) obtained from shoots grown on selection medium were cultured on BM which contained BAP (4 mg/l), NAA (0.5 mg/l), and hygromycin (10 mg/l) for 3–4 weeks. Those leaf sections which remained green, and produced callus, roots, or shoots, were determined to originate from transgenic plants. Nontransformed tissue (or "escapes") turned brown and died.

b. Polymerase Chain Reaction: DNA

The presence of a gene may be determined by assaying for the presence of its DNA in a tissue sample. Two such assay methods include a Polymerase Chain Reaction (PCR) assay and a Southern assay.

A Polymerase Chain Reaction (PCR) assay was utilized to analyze very small amounts of DNA for the presence of two genes, the yeast desaturase coding region (SEQ ID NO:1), and the HPT gene (which confers hygromycin resistance). Only 100 ng of DNA isolated from rapeseed leaf tissue was assayed per sample essentially as described (in Current Protocols in Molecular Biology (1987) edited by Ausubel, RM et al; Greene Publishing Associates & Wiley-Interscience). Primers corresponding to positions +543 and +1277 in the coding sequence of the yeast desaturase gene (SEQ ID NO:1) resulted in the synthesis of a DNA fragment which appeared as a 751 bp band in those plants which contained the gene. In a similar fashion, primers to specific sections of the HPT gene resulted in the synthesis of a DNA fragment in those plants which contained the HPT gene.

c. Southern Analysis

A Southern analysis detects the presence of a specific sequence of DNA in a sample by hybridization of a labelled probe to that sequence in the sample DNA. Much more DNA is required for the analysis than is needed for a PCR assay (see above). The number of copies of the yeast desaturase gene (SEQ ID NO:1) transferred into transformed rapeseed plants can also be determined from Southern analysis.

10 ug of DNA per sample isolated from rapeseed tissue was digested with HindIII and subjected to Southern analysis essentially as described (Current Protocols in Molecular Biology (1987) edited by Ausubel, RM et al; Greene Publishing Associates & Wiley-Interscience). A 402 bp and 422 bp EcoR1 doublet from the coding sequence of the yeast desaturase gene (SEQ ID NO:2) was labelled by the random hexamer procedure according to the manufacturer's instructions (United States Biochemical) and used as a probe.

EXAMPLE 6

Expression of Yeast delta-9 Desaturase in Seed Tissue

The expression of the yeast delta-9 desaturase in seed tissue results in transcription of the DNA to mRNA; the mRNA is in turn translated into the protein. Finally, the active protein desaturates saturated fatty acids. Thus, determination of expression of the yeast delta-9 desaturase gene (SEQ ID NO:1) in seed tissue may be determined by assaying for the presence of either mRNA, the protein (SEQ ID NO:2), or an altered fatty acid composition in the seed oil.

a. Polymerase Chain Reaction: mRNA

Expression of the yeast desaturase gene (SEQ ID NO:1) is determined at the level of transcription by detecting the presence of the desaturase mRNA. This is accomplished by a linked reverse transcription and PCR assay modified from Frohman et al (1988; PNAS (USA) 85: 8998–9002) in which small amounts of tissue are analyzed for the presence of RNA transcripts from the desaturase gene (SEQ ID NO:1).

b. Western Analysis

A Western analysis detects the presence of a protein by binding the protein, after separation by gel electrophoresis, to a labelled antibody. Thus, this method detects expression of a gene at the level of translation, or the protein level. It is preferable to assay the tissue when the highest level of expression of the gene is expected, for example, during oil accumulation during seed development.

Seeds from transgenic plants are collected at various times after pollination. Protein samples are prepared from pools of 10 seeds for each plant by homogenizing in SDS gel buffer (50mM Tris-HCl,pH 6.8, 1% SDS, 2 mM DTF and 2 mM EDTA). The homogenates are clarified by spinning in a microcentrifuge for 5 min. The proteins in the supernatant fractions are separated by 10% SDS-PAGE (Laemmli, UK (1970) Nature 227: 680–685), transferred to a nitrocellulose membrane (Towbin, H et al. (1979) Proc.Natl.Acd.Sci.USA 76: 4350–4354) and reacted sequentially with first rabbit polyclonal antiserum raised to a yeast desaturase peptide and then with anti-rabbit enzyme-conjugated (either alkaline phosphatase or horse radish peroxidase) IgG. The conjugated antibodies are visualized by activity staining according to the manufacturer's protocol(s).

c. Fatty Acid Analysis

The fatty acid composition of rapeseed was determined as described below for either "half-seed" analysis, "single/whole seed" analysis, or "bulk seed" analyses (for example, the fatty acid methylation procedure is a modification of that reported Craig, B. M. and Murty, N. L., 1959, J Amer Oil Chem Soc 36: 549–552).

For "half-seed" analyses, a portion of cotyledonary tissue from the embryo was removed and analyzed; the remaining seed was then saved, and could be germinated if desired.

1. The sample of cotyledonary tissue was placed into a 2 ml autosampler vial.

2. n-Heptane (500 ul) was added, and the oil extracted for 16 hours by incubation at room temperature.

3. Sodium methoxide in methanol (50 ul of 0.5M) was added, and the fatty acids transesterified for 60 minutes at room temperature.

4. Distilled water (20 ul) was then added, and the vial capped with a TPFE lined crimp top cap. The sample was thus ready to be processed through the gas liquid chromatograph. For "single-seed" analyses, a single seed was placed in a 2.0 ml autosampler vial and crushed with a glass rod.

1. n-Heptane (1.0 ml) was added, and the oil extracted for 16 hours by incubation at room temperature.

2. n-Heptane (3.0 ml) was added, and the oil extracted for one hour by incubation at room temperature.

3. Sodium methoxide in methanol (50 ul of 0.5N) was added, the vial vortexed, and the fatty acids transesterified for 60 minutes at room temperature.

4. Distilled water (20 ul) was added, the vial was vortexed and then capped with a TPFE crimp top cap. The sample was thus ready to be processed through the gas liquid chromatograph. For "bulk-seed" analyses, six mature seeds were selected which were black in color and well filled.

1. The seeds were placed in a 16×100 mm disposable glass test tube.

2. n-Heptane (1.5 ml) was added, and the seeds ground with a tissue homogenizer. The oil was extracted for one minute.

3. Sodium methoxide in methanol (500 ul of 0.5N) was added, the tube vortexed, and the sample incubated for 5 minutes.

4. Distilled water (7.0 ml) was added, and the tube vortexed.

5. A portion of the organic layer (1.5 ml) was transferred to a 2.0 ml autosampler vial, and the vial then capped with a TPFE crimp top cap. The sample was thus ready to be processed through the gas liquid chromatograph.

The GLC analyses were accomplished with a Hewlett Packard 5890 gas liquid chromatograph equipped with a flame ionization detector and a ChromStation integrator. A Hewlett Packard 7376 autosampler was used to withdraw a 1 ul portion of the methylated free fatty acids from the upper organic phase in the vial and to inject it into the GLC. The column used was a DB-23 fused silica capillary column (with a film thickness of 0.24 microns and column dimensions of 0.25 mm inner diameter×30 mm long).

The operating conditions for the GLC analysis included an injector temperature of 250° C. and a detector temperature of 300° C. The carrier gas was helium flowing at 1.1 cm3/minute through the column, and at 30 cm3/minute through the detector. Each chromatographic run began at 180° C. for 8 minutes; the temperature was then increased by 5° C. per minute to 220° C., and then held at 220° C. for 4 minutes. With this program, all of the major fatty acid methyl esters expected for vegetable oils (ie, palmitate, stearate, oleate, linoleate, and linolenate) had eluted; in addition, the two isomers of the monounsaturated 18-carbon fatty acid methyl ester, oleate and cis-vaccenate, were separated from each other. The proportion of each fatty acid present was expressed as the percent by weight relative to the total fatty acid content of the seed.

EXAMPLE 7

Transformed Plants

The rapeseed B. napus Profit is a spring Canola-type rapeseed with a high oleate content in the seed oil. Analysis of fifty individual seeds results in the following fatty acid profile:

TABLE 1 a. Fatty Acid Profile of B. napus cv Profit

| FATTY ACID | MEAN | MINIMUM | MAXIMUM |
| --- | --- | --- | --- |
| C16:0 | 4.05 | 3.20 | 7.40 |
| C16:1 | 0.18 | 0.00 | 0.50 |
| C18:0 | 2.07 | 1.20 | 3.80 |
| C18:1D9 | 63.78 | 51.90 | 72.10 |
| C18:1D11 | 2.72 | 1.80 | 5.90 |
| C18:2 | 16.76 | 11.50 | 21.80 |
| C18:3 | 6.82 | 3.60 | 11.20 |
| C20:0 | 0.73 | 0.50 | 1.30 |
| C20:1 | 1.24 | 0.90 | 1.50 |
| C22:0 | 0.38 | 0.00 | 0.80 |
| C24:0 | 0.24 | 0.00 | 0.90 |
| C24:1 | 0.21 | 0.00 | 0.40 | b. Fatty Acid Profile of regenerate B. napus cv Profit

| FATTY ACID | MEAN | MINIMUM | MAXIMUM |
| --- | --- | --- | --- |
| C16:0 | 5.28 | 4.30 | 6.90 |
| C16:1 | 0.26 | 0.10 | 0.50 |
| C18:0 | 1.78 | 1.20 | 3.60 |
| C18:1D9 | 51.51 | 40.70 | 63.70 |
| C18:1D11 | 2.39 | 1.40 | 3.70 |
| C18:2 | 25.35 | 16.30 | 35.00 |
| C18:3 | 9.68 | 4.80 | 18.20 |
| C20:0 | 0.66 | 0.40 | 1.30 |
| C20:1 | 1.08 | 0.80 | 1.40 |
| C22:0 | 0.40 | 0.20 | 0.90 |
| C24:0 | 0.30 | 0.00 | 0.70 |
| C24:1 | 0.29 | 0.00 | 0.70 |

Tissue obtained from Profit was transformed with each of four vectors as described above. The rooted transformed plants were transferred to soil when the shoots were 2 cm or more long. The plants were maintained in a Conviron growth chamber at 20° C. with 16 hours of light at 15° C. for 3–4 weeks; they were then moved into the greenhouse, where they were grown to maturity. Upon flowering, the plants were self-pollinated, and mature seed collected.

The fatty acid content of the resulting oil in the mature seeds is analyzed by either whole seed analysis, or by half-seed analysis in which a portion of the cotyledon is analyzed while the remaining seed is saved and can be planted.

Alternatively, in order to detect the presence of the yeast delta-9 desaturase protein (SEQ ID NO:2) in the seed, developing seeds are collected, and either mRNA is analyzed by a PCR assay or protein is assayed by a Western assay.

The fatty acid content of seeds obtained from rapeseed tissue transformed with the third vector, pH.PdeltaBOP, which was then regenerated and self-pollinated, contains a significant decrease in the proportions of the saturated fatty acids palmitate and stearate, with a concomitant increase in the levels of palmitoleate and oleate, when compared to the proportions observed in the non-transformed "parent" plant (see Table 1). In this vector, the yeast desaturase gene (SEQ ID NO:1) is placed under control of a modified phaseolin promoter. The modification, which consists of deleting the first ⅔ of the promoter, results in earlier expression of the regulated gene during seed development. Gene expression appears to occur during lipid accumulation, such that the unsaturated fatty acids are desaturated during triglycerol assembly. The resulting vegetable oil, with very low levels of saturated fatty acids, is a desirable substitute for vegetable oils currently on the market.

The fatty acid content of seeds obtained from plants transformed with any of the three other vectors, which are then regenerated and self-pollinated, contain varying proportions of the saturated fatty acids palmitate and stearate, which, however, are all equal to or lower than that observed in the non-transformed "parent" plant (see Table 1). These vectors, which contain regulatory elements which cause gene expression during seed development, result in variable levels of gene expression during lipid accumulation.

The seeds resulting from transformed, regenerated and self-pollinated plants are germinated and then self-pollinated upon flowering. The resulting seeds are then analyzed to determine trait stability and gene inheritance.

EXAMPLE 8

Transfer of Yeast delta-Desaturase Gene into Other Brassica

The yeast delta-9 desaturase gene is transferred to other Brassica by one of two methods. One is to directly transform other rapeseed and oilseed mustard as described above, and the other is to move the trait into other rapeseed and oilseed mustard by classical breeding techniques. Brassica rapa, Brassica napus, and Brassica junceae are suitable plants for plant transformation (see above). In addition, they may be intermated in a breeding program.

This allows the transfer of the yeast delta-9 desaturase gene (SEQ ID NO:1) to rapeseed and oilseed mustard selected on the basis of their initial fatty acid profiles or their agronomic characteristics. Some examples of rapeseed and oilseed mustard to which the yeast delta-9 desaturase gene (SEQ ID NO:1) is transferred are summarized in Table 2.

TABLE 2

Brassica cultivars to which yeast delta-nine desaturase gene (SEQ ID NO:1) is transferred Brassica napus

| | |
|---|---|
| Spring Canola | Profit, Excel, Legend, Delta, proprietary high oleate/low linoleate strains |
| Spring HEAR | Hero |
| Winter Canola | Ceres, Tapidor, Samoris, proprietary high oleate and high oleate/low linoleate strains |
| Winter HEAR | Bridger, LEI *Brassica rapa* |
| Spring Canola | Parkland, Colt, Horizon, Svalof High palmitate, proprietary high oleate strains |
| Spring HEAR | R500 *Brassica junceae* |
| Indian oilseed type High erucate | RH30, Puva Bold |
| Canadian oilseed type Low erucate | ZEM 87-1 |

The present invention has of necessity been discussed herein by reference to certain specific methods and materials. The enumeration of these methods and materials was merely illustrative, and in no way constitutes any limitation on the scope of the present invention. It is to be expected that those skilled in the art may discern and practice variations of or alternatives to the specific teachings provided herein, without departing from the scope of the present invention.

What we claim is:

1. A plant seed comprising DNA encoding yeast delta-9 desaturase and means for expressing said DNA in said plant seed.

2. The plant seed as defined by claim 1, wherein said means for expressing comprises a promoter effective to cause expression of said DNA in said plant seed.

3. The plant seed as defined by claim 2, wherein said promoter is a seed-specific promoter.

4. The plant seed as defined by claim 1, further comprising a termination sequence for said DNA.

5. The plant seed as defined by claim 4, wherein said termination sequence is selected from the group consisting of a yeast delta-9 desaturase termination sequence (SEQ ID NO:1), a phaseolin 3' termination sequence, and an ORF 25 3' termination sequence.

6. The plant seed as defined by claim 1, wherein said plant seed is a seed of a monocot plant genus.

7. The plant seed as defined by claim 6, wherein said monocot plant genus is selected from the group consisting of Zea and Sorghum.

8. The plant seed as defined by claim 1, wherein said plant seed is a seed of a dicot plant genus.

9. The plant seed as defined by claim 8, wherein said dicot plant genus is selected from the group consisting of Brassica, Helianthus, Carthamus, Sesamum, Glycine, Arachis, Gossypium, Lesquerella, and Vernonia.

10. The plant seed as defined by claim 9, further wherein said plant seed is a seed selected from the group consisting of Brassica rapa and Brassica napus.

11. A method for providing a modified fatty acid content of the seed oil of a plant seed, said method comprising the step of providing a transgenic plant seed comprising DNA encoding yeast delta-9 desaturase, wherein said DNA is expressed, whereby the fatty acid content is modified relative to the seed oil of non-transgenic plant seed.

12. The method as defined by claim 11, wherein said modification comprises an increase in the percent content of monounsaturated fatty acid in the seed oil of said plant seed.

13. The method as defined by claim 12, wherein said monounsaturated fatty acid has a carbon chain length of from 16 to 24 carbon atoms.

14. The method as defined by claim 13, wherein said monounsaturated fatty acid is selected from the group consisting of cis-9-hexadecanoic acid (palmitoleic acid), cis-9-octadecanoic acid (oleic acid), cis-11-octadecenoic acid (cis-vaccenic acid), cis-11-eicosenoic acid, cis-13-eicosenoic acid, cis-13-docosenoic acid, cis-15-docosenoic acid, cis-15-tetracosenoic acid, cis-17-tetracosenoic acid, and combinations thereof.

15. The method as defined by claim 11, wherein said modification comprises a reduction in the percent content of saturated fatty acid in the seed oil of said plant seed.

16. The method as defined by claim 15, wherein said saturated fatty acid is selected from the group consisting of myristic acid, palmitic acid, stearic acid, eicosanoic acid, docosanoic acid, tetracosanoic acid, and combinations thereof.

17. The method as defined by claim 15, wherein said plant seed is a seed of a monocot plant genus.

18. The method as defined by claim 17, wherein said monocot plant genus is selected from the group consisting of Zea and Sorghum.

19. The method as defined by claim 11, wherein said plant seed is a seed of a dicot plant genus.

20. The method seed as defined by claim 19, wherein said dicot plant genus is selected from the group consisting of Brassica, Helianthus, Carthamus, Sesamum, Glycine, Arachis, Gossypium, Lesquerella, and Vernonia.

21. The method as defined by claim 20, further wherein said plant seed is a seed selected from the group consisting of Brassica rapa and Brassica napus.

22. The method as defined by claim 11, wherein said step of providing comprises transforming a plant cell to contain exogenous DNA encoding yeast delta-9 desaturase, culturing said cell under conditions whereby a plant is regenerated therefrom, and maintaining said plant under conditions whereby said plant produces transgenic seed.

23. The method as defined by claim 22, wherein said step of transforming is carried out using transformation mediation selected from the group consisting of Agrobacterium, electroporation, polyethylene glycol (PEG), silicon carbide fiber, particle gun, and direct injection.

24. The method as defined by claim 23, further comprising constructing a vector containing DNA encoding yeast delta-9 desaturase and a promoter, placing said vector into a selected strain of Agrobacterium, and treating selected plant cells with said Agrobacterium under conditions sufficient to result in transfer of at least some of said vectors from said Agrobacterium to said plant cells, whereby said DNA is expressed in said plant cells.

25. A plant obtained from the plant seed as defined by claim 1, wherein the seeds of said plant comprise a DNA encoding yeast delta-9 desaturase and means for expressing said DNA in said plant seed.

* * * * *

UNITED STATES PATENT AND TRADEMARK OFFICE
CERTIFICATE OF CORRECTION

PATENT NO. : 5,777,201
DATED : July 7, 1998
INVENTOR(S) : Candace Gloria Poutre, Asha Mchra-Palta It is certified that error appears in the above-identified patent and that said Letters Patent is hereby corrected as shown below:

Column 15, line 9: "2 mM DTF" should read --2 mM DTT--.

Column 26, line 31: "The method seed as" should read --The method as--.

Signed and Sealed this

Thirty-first Day of August, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1782 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Saccharomyces cerevisiae
        ( B ) STRAIN: X2180-1A ( i x ) FEATURE:

-continued (A) NAME/KEY: CDS
(B) LOCATION: 106..1635

(xi) SEQUENCE DESCRIPTION: SEQ ID NO:1:

```
TACTTCTGTT TCCGTTTATA TTTTGTATTA CGTAGAATAG AACATCATAG TAATAGATAG          60

TTGTGGTGAT CATATTATAA ACAGCACTAA AACATTACAA CAAAG ATG CCA ACT            114
                                                 Met Pro Thr
                                                  1

TCT GGA ACT ACT ATT GAA TTG ATT GAC GAC CAA TTT CCA AAG GAT GAC          162
Ser Gly Thr Thr Ile Glu Leu Ile Asp Asp Gln Phe Pro Lys Asp Asp
     5              10                  15

TCT GCC AGC AGT GGC ATT GTC GAC GAA GTC GAC TTA ACG GAA GCT AAT          210
Ser Ala Ser Ser Gly Ile Val Asp Glu Val Asp Leu Thr Glu Ala Asn
 20              25                  30                  35

ATT TTG GCT ACT GGT TTG AAT AAG AAA GCA CCA AGA ATT GTC AAC GGT          258
Ile Leu Ala Thr Gly Leu Asn Lys Lys Ala Pro Arg Ile Val Asn Gly
             40                  45                  50

TTT GGT TCT TTA ATG GGC TCC AAG GAA ATG GTT TCC GTG GAA TTC GAC          306
Phe Gly Ser Leu Met Gly Ser Lys Glu Met Val Ser Val Glu Phe Asp
                 55                  60                  65

AAG AAG GGA AAC GAA AAG AAG TCC AAT TTG GAT CGT CTG CTA GAA AAG          354
Lys Lys Gly Asn Glu Lys Lys Ser Asn Leu Asp Arg Leu Leu Glu Lys
         70                  75                  80

GAC AAC CAA GAA AAA GAA GAA GCT AAA ACT AAA ATT CAC ATC TCC GAA          402
Asp Asn Gln Glu Lys Glu Glu Ala Lys Thr Lys Ile His Ile Ser Glu
             85                  90                  95

CAA CCA TGG ACT TTG AAT AAC TGG CAC CAA CAT TTG AAC TGG TTG AAC          450
Gln Pro Trp Thr Leu Asn Asn Trp His Gln His Leu Asn Trp Leu Asn
100                 105                 110                 115

ATG GTT CTT GTT TGT GGT ATG CCA ATG ATT GGT TGG TAC TTT GCT CTC          498
Met Val Leu Val Cys Gly Met Pro Met Ile Gly Trp Tyr Phe Ala Leu
                    120                 125                 130

TCT GGT AAA GTG CCT TTG CAT TTA AAC GTT TTC CTT TTC TCC GTT TTC          546
Ser Gly Lys Val Pro Leu His Leu Asn Val Phe Leu Phe Ser Val Phe
         135                 140                 145

TAC TAC GCT GTC GGT GGT GTT TCT ATT ACT GCC GGT TAC CAT AGA TTA          594
Tyr Tyr Ala Val Gly Gly Val Ser Ile Thr Ala Gly Tyr His Arg Leu
150                 155                 160

TGG TCT CAC AGA TCT TAC TCC GCT CAC TGG CCA TTG AGA TTA TTC TAC          642
Trp Ser His Arg Ser Tyr Ser Ala His Trp Pro Leu Arg Leu Phe Tyr
    165                 170                 175

GCT ATC TTC GGT TGT GCT TCC GTT GAA GGG TCC GCT AAA TGG TGG GGC          690
Ala Ile Phe Gly Cys Ala Ser Val Glu Gly Ser Ala Lys Trp Trp Gly
180                 185                 190                 195

CAC TCT CAC AGA ATT CAC CAT CGT TAC ACT GAT ACC TTG AGA GAT CCT          738
His Ser His Arg Ile His His Arg Tyr Thr Asp Thr Leu Arg Asp Pro
                    200                 205                 210

TAT GAC GCT CGT AGA GGT CTA TGG TAC TCC CAC ATG GGA TGG ATG CTT          786
Tyr Asp Ala Arg Arg Gly Leu Trp Tyr Ser His Met Gly Trp Met Leu
             215                 220                 225

TTG AAG CCA AAT CCA AAA TAC AAG GCT AGA GCT GAT ATT ACC GAT ATG          834
Leu Lys Pro Asn Pro Lys Tyr Lys Ala Arg Ala Asp Ile Thr Asp Met
         230                 235                 240

ACT GAT GAT TGG ACC ATT AGA TTC CAA CAC AGA CAC TAC ATC TTG TTG          882
Thr Asp Asp Trp Thr Ile Arg Phe Gln His Arg His Tyr Ile Leu Leu
245                 250                 255

ATG TTG TTA ACC GCT TTC GTC ATT CCA ACT CTT ATC TGT GGT TAC TTT          930
Met Leu Leu Thr Ala Phe Val Ile Pro Thr Leu Ile Cys Gly Tyr Phe
260                 265                 270                 275

TTC AAC GAC TAT ATG GGT GGT TTG ATC TAT GCC GGT TTT ATT CGT GTC          978
```

-continued

| | | | | | | | | | | | | | | | | |
|---|---|---|---|---|---|---|---|---|---|---|---|---|---|---|---|---|
| Phe | Asn | Asp | Tyr | Met 280 | Gly | Gly | Leu | Ile 285 | Tyr | Ala | Gly | Phe | Ile | Arg 290 | Val | |
| TTT Phe | GTC Val | ATT Ile | CAA Gln 295 | CAA Gln | GCT Ala | ACC Thr | TTT Phe | TGC Cys 300 | ATT Ile | AAC Asn | TCC Ser | TTG Leu | GCT Ala 305 | CAT His | TAC Tyr | 1026 |
| ATC Ile | GGT Gly | ACC Thr 310 | CAA Gln | CCA Pro | TTC Phe | GAT Asp | GAC Asp 315 | AGA Arg | AGA Arg | ACC Thr | CCT Pro | CGT Arg 320 | GAC Asp | AAC Asn | TGG Trp | 1074 |
| ATT Ile | ACT Thr 325 | GCC Ala | ATT Ile | GTT Val | ACT Thr | TTC Phe 330 | GGT Gly | GAA Glu | GGT Gly | TAC Tyr | CAT His 335 | AAC Asn | TTC Phe | CAC His | CAC His | 1122 |
| GAA Glu 340 | TTC Phe | CCA Pro | ACT Thr | GAT Asp | TAC Tyr 345 | AGA Arg | AAC Asn | GCT Ala | ATT Ile | AAG Lys 350 | TGG Trp | TAC Tyr | CAA Gln | TAC Tyr | GAC Asp 355 | 1170 |
| CCA Pro | ACT Thr | AAG Lys | GTT Val | ATC Ile 360 | ATC Ile | TAT Tyr | TTG Leu | ACT Thr | TCT Ser 365 | TTA Leu | GTT Val | GGT Gly | CTA Leu | GCA Ala 370 | TAC Tyr | 1218 |
| GAC Asp | TTG Leu | AAG Lys | AAA Lys 375 | TTC Phe | TCT Ser | CAA Gln | AAT Asn | GCT Ala 380 | ATT Ile | GAA Glu | GAA Glu | GCC Ala | TTG Leu 385 | ATT Ile | CAA Gln | 1266 |
| CAA Gln | GAA Glu | CAA Gln 390 | AAG Lys | AAG Lys | ATC Ile | AAT Asn | AAA Lys 395 | AAG Lys | AAG Lys | GCT Ala | AAG Lys | ATT Ile 400 | AAC Asn | TGG Trp | GGT Gly | 1314 |
| CCA Pro | GTT Val 405 | TTG Leu | ACT Thr | GAT Asp | TTG Leu | CCA Pro 410 | ATG Met | TGG Trp | GAC Asp | AAA Lys | CAA Gln 415 | ACC Thr | TTC Phe | TTG Leu | GCT Ala | 1362 |
| AAG Lys 420 | TCT Ser | AAG Lys | GAA Glu | AAC Asn | AAG Lys 425 | GGT Gly | TTG Leu | GTT Val | ATC Ile | ATT Ile 430 | TCT Ser | GGT Gly | ATT Ile | GTT Val | CAC His 435 | 1410 |
| GAC Asp | GTA Val | TCT Ser | GGT Gly | TAT Tyr 440 | ATC Ile | TCT Ser | GAA Glu | CAT His | CCA Pro 445 | GGT Gly | GGT Gly | GAA Glu | ACT Thr | TTA Leu 450 | ATT Ile | 1458 |
| AAA Lys | ACT Thr | GCA Ala | TTA Leu 455 | GGT Gly | AAG Lys | GAC Asp | GCT Ala | ACC Thr 460 | AAG Lys | GCT Ala | TTC Phe | AGT Ser | GGT Gly 465 | GGT Gly | GTC Val | 1506 |
| TAC Tyr | CGT Arg | CAC His 470 | TCA Ser | AAT Asn | GCC Ala | GCT Ala | CAA Gln 475 | AAT Asn | GTC Val | TTG Leu | GCT Ala | GAT Asp 480 | ATG Met | AGA Arg | GTG Val | 1554 |
| GCT Ala | GTT Val 485 | ATC Ile | AAG Lys | GAA Glu | AGT Ser | AAG Lys 490 | AAC Asn | TCT Ser | GCT Ala | ATT Ile | AGA Arg 495 | ATG Met | GCT Ala | AGT Ser | AAG Lys | 1602 |
| AGA Arg 500 | GGT Gly | GAA Glu | ATC Ile | TAC Tyr | GAA Glu 505 | ACT Thr | GGT Gly | AAG Lys | TTC Phe | TTT Phe 510 | TAAGTATCAC | | ATTACAATAA | | | 1655 |

CAAAACTGCA ACTACCATAA AAAAAAATTG AAAAATCATA AATTAAAAAA AAAAAAATCA 1715

ATTGAATTTT TTTTTTTCAT GATTACGTTT TGACATTTTT TCTTTTTTTT TCTCTTATTA 1775

CGATTTA 1782

( 2 ) INFORMATION FOR SEQ ID NO:2:

( i ) SEQUENCE CHARACTERISTICS:
        ( A ) LENGTH: 510 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Pro | Thr | Ser | Gly 5 | Thr | Thr | Ile | Glu | Leu 10 | Ile | Asp | Asp | Gln | Phe Pro 15 |

-continued

| | | | | | | | | | | | | | | |
|---|---|---|---|---|---|---|---|---|---|---|---|---|---|---|
| Lys | Asp | Asp | Ser<br>20 | Ala | Ser | Ser | Gly | Ile<br>25 | Val | Asp | Glu | Val<br>30 | Asp | Leu | Thr |
| Glu | Ala | Asn<br>35 | Ile | Leu | Ala | Thr | Gly<br>40 | Leu | Asn | Lys | Lys<br>45 | Ala | Pro | Arg | Ile |
| Val | Asn<br>50 | Gly | Phe | Gly | Ser | Leu<br>55 | Met | Gly | Ser | Lys | Glu<br>60 | Met | Val | Ser | Val |
| Glu<br>65 | Phe | Asp | Lys | Lys | Gly<br>70 | Asn | Glu | Lys | Lys | Ser<br>75 | Asn | Leu | Asp | Arg | Leu<br>80 |
| Leu | Glu | Lys | Asp | Asn<br>85 | Gln | Glu | Lys | Glu | Ala<br>90 | Lys | Thr | Lys | Ile<br>95 | His |
| Ile | Ser | Glu | Gln<br>100 | Pro | Trp | Thr | Leu | Asn<br>105 | Asn | Trp | His | Gln | His<br>110 | Leu | Asn |
| Trp | Leu | Asn<br>115 | Met | Val | Leu | Val | Cys<br>120 | Gly | Met | Pro | Met | Ile<br>125 | Gly | Trp | Tyr |
| Phe | Ala<br>130 | Leu | Ser | Gly | Lys | Val<br>135 | Pro | Leu | His | Leu | Asn<br>140 | Val | Phe | Leu | Phe |
| Ser<br>145 | Val | Phe | Tyr | Tyr | Ala<br>150 | Val | Gly | Gly | Val | Ser<br>155 | Ile | Thr | Ala | Gly | Tyr<br>160 |
| His | Arg | Leu | Trp | Ser<br>165 | His | Arg | Ser | Tyr | Ser<br>170 | Ala | His | Trp | Pro | Leu<br>175 | Arg |
| Leu | Phe | Tyr | Ala<br>180 | Ile | Phe | Gly | Cys | Ala<br>185 | Ser | Val | Glu | Gly | Ser<br>190 | Ala | Lys |
| Trp | Trp | Gly<br>195 | His | Ser | His | Arg | Ile<br>200 | His | His | Arg | Tyr | Thr<br>205 | Asp | Thr | Leu |
| Arg | Asp<br>210 | Pro | Tyr | Asp | Ala | Arg<br>215 | Arg | Gly | Leu | Trp | Tyr<br>220 | Ser | His | Met | Gly |
| Trp<br>225 | Met | Leu | Leu | Lys | Pro<br>230 | Asn | Pro | Lys | Tyr | Lys<br>235 | Ala | Arg | Ala | Asp | Ile<br>240 |
| Thr | Asp | Met | Thr | Asp<br>245 | Asp | Trp | Thr | Ile | Arg<br>250 | Phe | Gln | His | Arg | His<br>255 | Tyr |
| Ile | Leu | Leu | Met<br>260 | Leu | Leu | Thr | Ala | Phe<br>265 | Val | Ile | Pro | Thr | Leu<br>270 | Ile | Cys |
| Gly | Tyr | Phe<br>275 | Phe | Asn | Asp | Tyr | Met<br>280 | Gly | Gly | Leu | Ile | Tyr<br>285 | Ala | Gly | Phe |
| Ile | Arg<br>290 | Val | Phe | Val | Ile | Gln<br>295 | Gln | Ala | Thr | Phe | Cys<br>300 | Ile | Asn | Ser | Leu |
| Ala<br>305 | His | Tyr | Ile | Gly | Thr<br>310 | Gln | Pro | Phe | Asp | Asp<br>315 | Arg | Arg | Thr | Pro | Arg<br>320 |
| Asp | Asn | Trp | Ile | Thr<br>325 | Ala | Ile | Val | Thr | Phe<br>330 | Gly | Glu | Gly | Tyr | His<br>335 | Asn |
| Phe | His | His | Glu<br>340 | Phe | Pro | Thr | Asp | Tyr<br>345 | Arg | Asn | Ala | Ile | Lys<br>350 | Trp | Tyr |
| Gln | Tyr | Asp<br>355 | Pro | Thr | Lys | Val | Ile<br>360 | Ile | Tyr | Leu | Thr | Ser<br>365 | Leu | Val | Gly |
| Leu | Ala<br>370 | Tyr | Asp | Leu | Lys | Lys<br>375 | Phe | Ser | Gln | Asn | Ala<br>380 | Ile | Glu | Glu | Ala |
| Leu<br>385 | Ile | Gln | Gln | Glu | Gln<br>390 | Lys | Lys | Ile | Asn | Lys<br>395 | Lys | Lys | Ala | Lys | Ile<br>400 |
| Asn | Trp | Gly | Pro | Val<br>405 | Leu | Thr | Asp | Leu | Pro<br>410 | Met | Trp | Asp | Lys | Gln<br>415 | Thr |
| Phe | Leu | Ala | Lys<br>420 | Ser | Lys | Glu | Asn | Lys<br>425 | Gly | Leu | Val | Ile | Ile<br>430 | Ser | Gly |
| Ile | Val | His<br>435 | Asp | Val | Ser | Gly | Tyr<br>440 | Ile | Ser | Glu | His | Pro<br>445 | Gly | Gly | Glu |

| | | | | | | | | | | | | | | | |
|---|---|---|---|---|---|---|---|---|---|---|---|---|---|---|---|
| Thr | Leu 450 | Ile | Lys | Thr | Ala | Leu 455 | Gly | Lys | Asp | Ala | Thr 460 | Lys | Ala | Phe | Ser |
| Gly 465 | Gly | Val | Tyr | Arg | His 470 | Ser | Asn | Ala | Ala | Gln 475 | Asn | Val | Leu | Ala | Asp 480 |
| Met | Arg | Val | Ala | Val 485 | Ile | Lys | Glu | Ser | Lys 490 | Asn | Ser | Ala | Ile | Arg 495 | Met |
| Ala | Ser | Lys | Arg 500 | Gly | Glu | Ile | Tyr | Glu 505 | Thr | Gly | Lys | Phe | Phe 510 | | |